United States Patent
Chooi et al.

(10) Patent No.: US 6,419,754 B1
(45) Date of Patent: Jul. 16, 2002

(54) ENDPOINT DETECTION AND NOVEL CHEMICALS IN COPPER STRIPPING

(75) Inventors: Simon Chooi; Mei Sheng Zhou, both of Singapore (SG)

(73) Assignee: Chartered Semiconductor Manufacturting Ltd., Singapore (SG)

( * ) Notice: Subject to any disclaimer, the term of this patent is extended or adjusted under 35 U.S.C. 154(b) by 0 days.

(21) Appl. No.: 09/376,426

(22) Filed: Aug. 18, 1999

(51) Int. Cl.$^7$ ................................................. C23G 1/16
(52) U.S. Cl. .................. 134/2; 134/3; 134/18; 134/26; 134/34; 134/36; 134/41; 134/42; 436/55; 436/80
(58) Field of Search ............................ 134/2, 3, 18, 26, 134/34, 36, 41, 42; 436/55, 80

(56) References Cited

U.S. PATENT DOCUMENTS

| | | | |
|---|---|---|---|
| 3,615,246 A | * 10/1971 | Lindstrom | 23/273 |
| 3,951,602 A | * 4/1976 | Thompson | 23/230 R |
| 3,964,956 A | * 6/1976 | Snyder | 134/57 R |
| 4,286,965 A | 9/1981 | Vanhumbeeck et al. | 23/230 A |
| 4,315,518 A | * 2/1982 | Sawyer | 137/3 |
| 4,424,097 A | * 1/1984 | Lipka et al. | 156/656 |
| 4,749,552 A | 6/1988 | Sakisako et al. | 422/75 |
| 4,774,101 A | 9/1988 | Harris et al. | 427/8 |
| 5,059,243 A | * 10/1991 | Jagannathan et al. | 106/1.26 |
| 5,178,771 A | * 1/1993 | Hayashibe et al. | 210/709 |
| 5,259,920 A | * 11/1993 | Law | 156/626 |
| 5,294,554 A | * 3/1994 | Uchida et al. | 436/73 |
| 5,836,805 A | 11/1998 | Obeng | 451/36 |

OTHER PUBLICATIONS

Patel, eta l. "New indicator for titration of copper by EDTA", J. Inst. Chem., Calcutta (1975), 47, Pt. 5, 180–2, abstract only.*

Belcher, et al. Fast Sulfon Black F as an indicator for the EDTA titration of copper, Chem. & Ind. (London), 1957, 1647, abstract only.*

* cited by examiner

*Primary Examiner*—Sharidan Carrillo
(74) *Attorney, Agent, or Firm*—George O. Saile; Rosemary L. S. Pike

(57) ABSTRACT

An endpoint detection system for copper stripping using a colorimetric analysis of the change in concentration of a component is described. Wet copper stripping chemicals are used to strip copper from a wafer whereby an eluent is produced. The eluent is continuously analyzed by colorimetric analysis for the presence of copper. The copper stripping process is stopped when the presence of copper is no longer detected. Also novel compounds or chemicals for use in an endpoint detection system for copper stripping using a colorimetric analysis of the change in concentration of the novel compounds or chemicals are described. A composition of matter that serves as an indicator of the presence of copper by colorimetric analysis comprises: 1) Fast Sulphon Black F indicator and an ammonium ion-containing solution or 2) a complexing agent, comprising a diamine, an amine macrocycle, or a monoamine.

31 Claims, 3 Drawing Sheets

ENDPOINT DETECTION AND NOVEL CHEMICALS IN COPPER STRIPPING

BACKGROUND OF THE INVENTION (1) Field of the Invention

The invention relates to a method of copper stripping in the fabrication of integrated circuits, and more particularly, to a method of endpoint detection for controlled copper stripping in the manufacture of integrated circuits.

(2) Description of the Prior Art

In the manufacture of integrated circuits, copper stripping is required in a number of situations: after blanket copper deposition on a bare silicon wafer, after copper seed layer deposition in a damascene process, after electroplated copper deposition in a damascene process, or after copper chemical mechanical polishing (CMP), for example. Wet stripping of copper generally requires an extensive duration, or overstripping, as a safeguard to be sure that all of the copper is removed. Overstripping incurs a high cost. It is necessary to periodically measure the remaining copper thickness to determine when to stop the stripping process. This is time-consuming. It is desired to provide an endpoint detection system for copper stripping.

U.S. Pat. No. 5,836,805 to Obeng discloses a method of examining the waste slurry of a chemical mechanical polishing (CMP) process to determine the endpoint. Conductivity, luminescence, or particulate mass are measured depending upon the material being polished. U.S. Pat. No. 4,774,101 to Harris et al controls the contents of an electroless copper plating bath by optical means. U.S. Pat. No. 4,286,965 to Vanhumbeeck et al also controls the contents of an electroless copper plating bath. The amount of copper in the bath is measured by colorimeter. U.S. Pat. No. 4,749,552 to Sakisako et al automatically maintains the density of an etching liquid used to etch a specific quantity of copper. Measurements of the etching liquid's contents are made by titration.

SUMMARY OF THE INVENTION

A principal object of the present invention is to provide an effective and very manufacturable method of endpoint detection for copper stripping in the fabrication of integrated circuit devices.

Another object of the invention is to provide an endpoint detection system for copper stripping on a single wafer system or a batch wafer system.

Yet another object of the invention is to provide an endpoint detection system for copper stripping using a colorimetric or spectrophotometric analysis of the change in concentration of a component.

Yet another object of the invention is to provide novel compounds or chemicals for use in an endpoint detection system for copper stripping.

Yet another object of the invention is to provide novel compounds or chemicals for use in an endpoint detection system for copper stripping using a colorimetric or spectrophotometric analysis of the change in concentration of the novel compounds or chemicals.

In accordance with the objects of this invention an endpoint detection system for copper stripping using a colorimetric or spectrophotometric analysis of the change in concentration of a component is achieved. Wet copper stripping chemicals are used to strip copper from a wafer whereby an eluent is produced. The eluent is continuously analyzed by colorimetric or spectrophotometric analysis for the presence of copper. The copper stripping process is stopped when the presence of copper is no longer detected.

Also in accordance with the objects of the invention, novel compounds or chemicals for use in an endpoint detection system for copper stripping using a colorimetric or spectrophotometric analysis of the change in concentration of the novel compounds or chemicals are provided. A composition of matter that serves as an indicator of the presence of copper by colorimetric analysis comprises: 1) Fast Sulphon Black F indicator and an ammonium ion-containing solution or 2) a complexing agent, comprising a diamine, an amine macrocycle, or a monoamine.

BRIEF DESCRIPTION OF THE DRAWINGS

In the accompanying drawings forming a material part of this description, there is shown.

DESCRIPTION OF THE PREFERRED EMBODIMENTS

Figure 1:
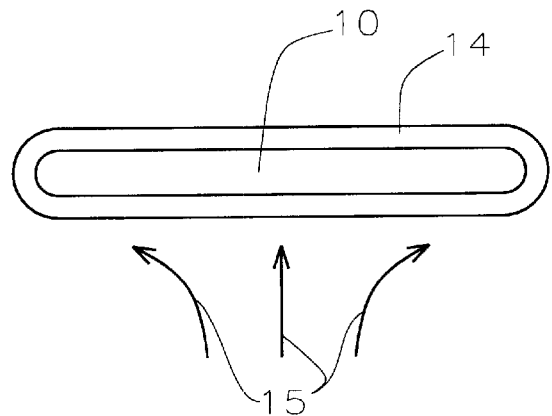
FIGS. 1 through 4 schematically illustrate in cross-sectional representation ways of copper stripping.
Figure 2:
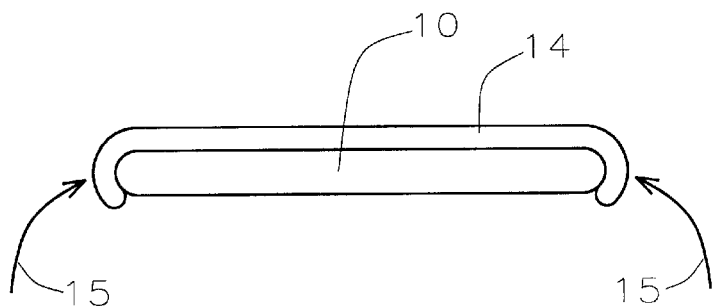
Figure 3:
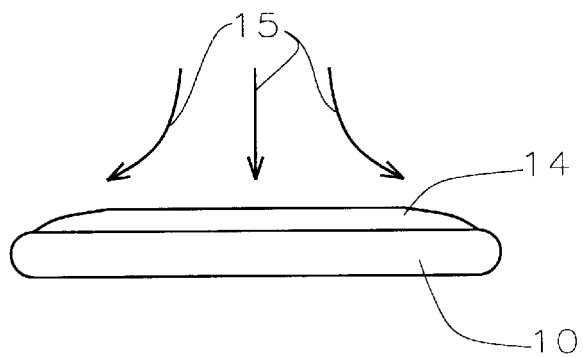
Figure 4:
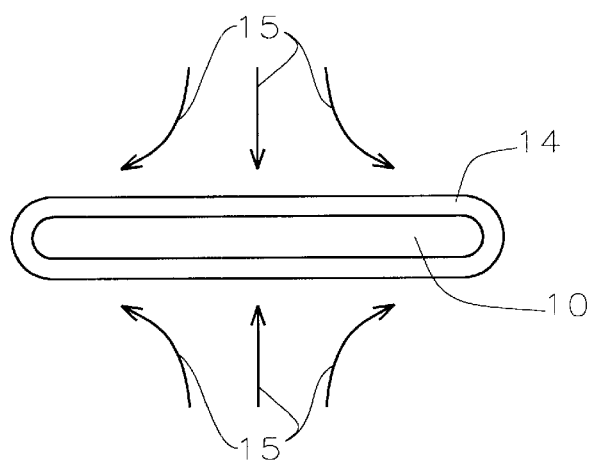

Copper stripping is performed in a variety of ways. FIGS. 1 through 4 illustrate a wafer 10 having a coating of copper 14 thereover. Stripping is indicated by arrows 15. For example, as shown in FIG. 1, copper 14 may be removed from the backside of the wafer only. FIG. 2 illustrates edge exclusive copper stripping where copper is removed at the bevel. FIG. 3 illustrates frontside copper stripping and FIG. 4 illustrates both frontside and backside stripping.

Figure 5:
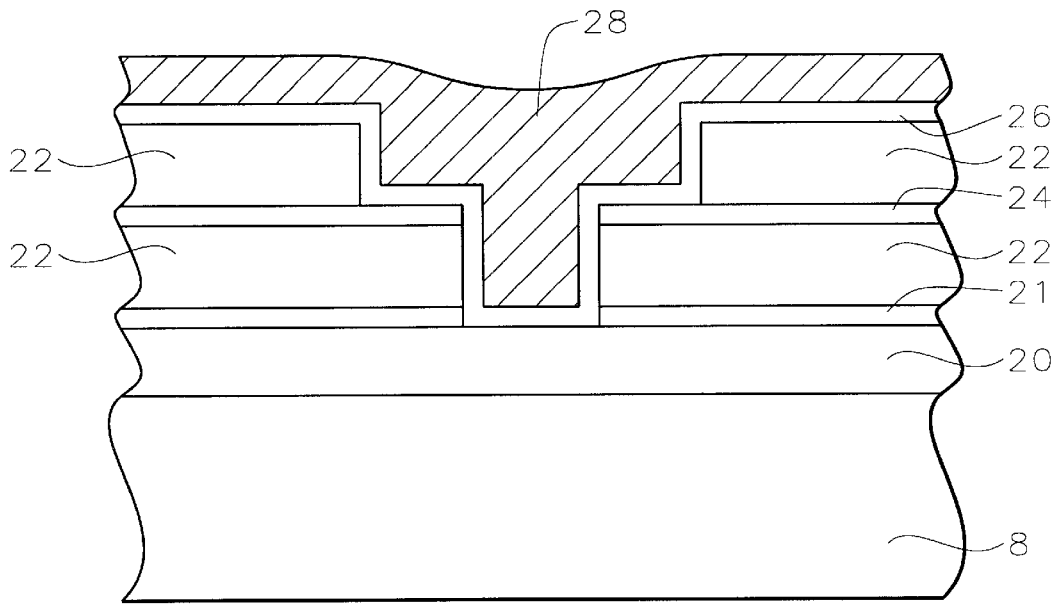
FIG. 5 schematically illustrates copper stripping in a dual damascene process.

For example, FIG. 5 illustrates a partially completed integrated circuit device. A first copper interconnect 20 has been formed on a semiconductor substrate 8. A dual damascene opening has been made through dielectric layers 22 and passivation and etch stop layers 21 and 24, respectively. A barrier metal layer 26, comprising tantalum or tantalum nitride, for example, has been deposited over the topmost dielectric layer and within the dual damascene opening. Copper layer 28 has been deposited by any of the conventional methods, such as by copper seed layer, or electro- or electroless plating. Now the excess copper 28 is to be stripped. The process of the invention provides a method for endpoint detection for such copper stripping.

The process of the invention proposes an endpoint detection system for any of the various copper stripping applications in a single wafer system or in a batch wafer system where the stripping chemicals go directly to the drain. The invention proposes the insertion of a colorimetric or spectrophotometric detector just after the chemicals exit the processing chamber and before they enter the drain. A colorimeter determines the concentration of a substance by measuring the relative absorption of light by the substance and comparing that measurement to a known concentration of the substance. A spectrophotometer produces a signal corresponding to the difference between the transmitted radiation of a reference material and that of a sample at selected wavelengths of radiation possessing a bandwidth of 1 nanometer. It is made up of an optical spectrometer and a photometer.

Figure 6:
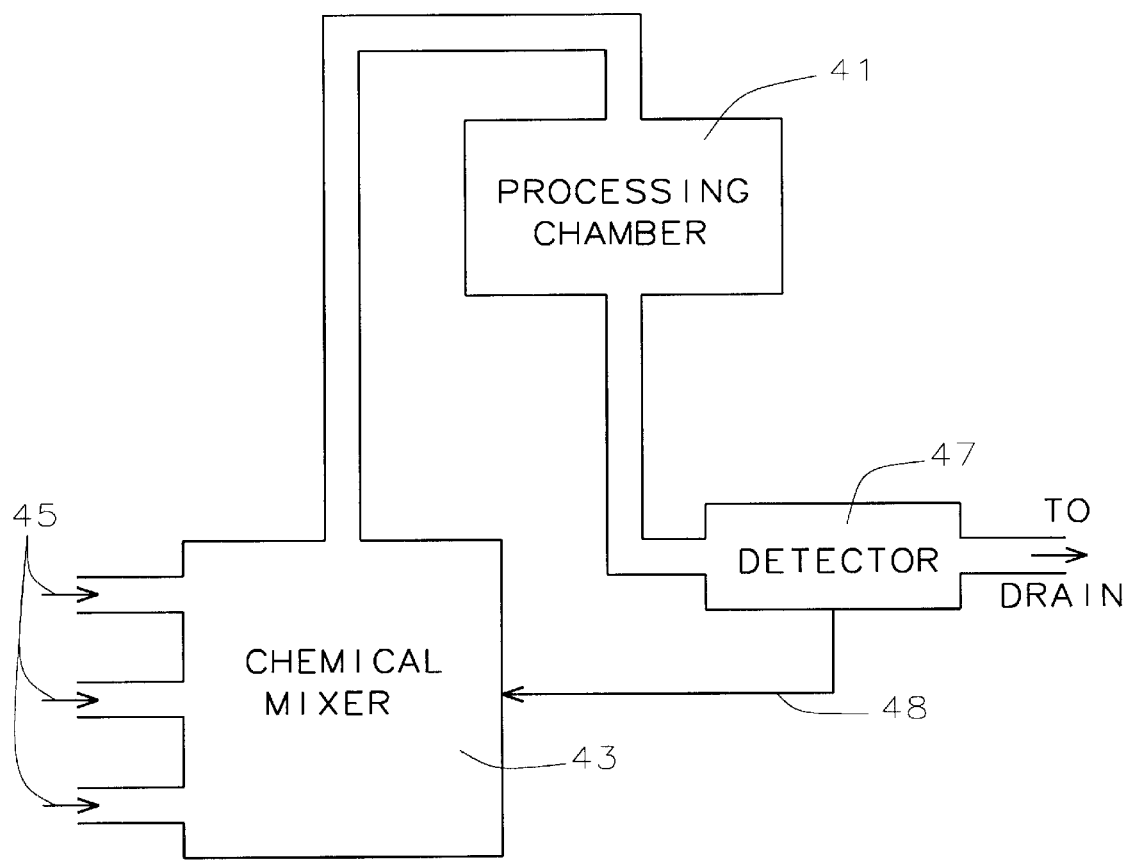
FIG. 6 schematically illustrates in cross-sectional representation copper stripping equipment including the endpoint detection system of the present invention.

FIG. 6 illustrates a schematic of the proposed copper stripping system with endpoint detection. Copper stripping occurs in the processing chamber 41. Stripping chemicals are mixed in the Chemical Mixer 43. Chemicals enter through valves 45. The copper stripping equipment including chemical mixer and processing chamber may include any of the standard equipment including the SEZ single wafer etcher, Semitool Millenium, FSI Mercury, Zeta, and so on. The endpoint detection is that of a colorimetric or spectrophotometric analysis where the variation of the color of the system with a change in the concentration of some component is detected. The colorimetric or spectrophotometric detector 47 analyzes the eluent from the processing chamber on its way to the drain.

The gradual desired removal of copper leads to a gradual decrease in color intensity of the eluent. Once a preset target value is reached (that is, no color is detected), the detector sends a signal 48 to the chemical mixer 43 to stop the flow of chemicals and thus to stop the copper stripping process.

Although copper(II) salts are blue; for example copper(II) sulfate, their spectroscopic absorption coefficients are not strong enough to be detected by the colorimeter or the spectrophotometer. In order to increase the absorption coefficient (and sensitivity) for use on the spectrophotometer or colorimeter, the addition of novel compounds/chemicals is necessary, instead of such typical chemicals such as nitric acid and sulfuric acid.

Two methodologies for increasing the absorption coefficient of the stripping chemicals are proposed. In the first embodiment, small amounts of Fast Sulphon Black F indicator are introduced as one of the chemicals for copper stripping. The indicator is very specific in its color reaction with copper in ammonical solutions: it forms a red complex. Hence, an ammonium ion-containing solution is also to be introduced into the chemical mixer. Ammonium ion-containing solutions include: ammonium acetate, ammonium carbonate, ammonium hydroxide, ammonium nitrate, ammonium perchlorate, ammonium sulfate, ammonium tetrafluoroborate, ammonium trifluoroacetate, ammonium trifluoromethanesulfonate[$NH_4(CF_3SO_3)$], and a mixture of ammonium fluoride, water, and ethylenediamine. The indicator will comprise less than 10% of the total volume of the solution while the ammonium containing solution will comprise the remaining 90% or more.

In the second embodiment of the invention, small amounts of complexing agents are added to the stripping chemicals, such as nitric acid or sulfuric acid, in the chemical mixer 43. These complexing agents may be diamines, amine macrocycles, or monoamines. The complexing agents coordinate to copper forming complexes that have an increased spectroscopic absorbence coefficient. The complexing agents will comprise less than 10% of the total volume of solution.

For example, diamines may include $H_2NCH_2CH_2N(C_2H_5)_2$(ethylenediamine), $(C_2H_5)_2NCH_2CH_2N(C_2H_5)_2$, (N,N,N',N'-tetraethylenediamine),

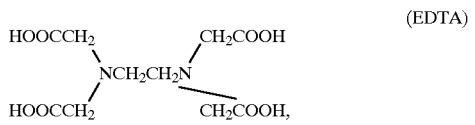

(EDTA)

1,10-phenanthroline, and 2,2'-bipyridine-4,4'-dicarboxylic acid.

For example, amine macrocycles may include: 1,4,8-Triazacycloundecane, 1,4,8,11-Tetramethyl-1,4,8,11-tetraazacyclotetradecane, 3,8,13,18-tetramethyl-21H,23H-porphine-2,7,12,17-tetraprapionic acid dihydrochloride, and many others.

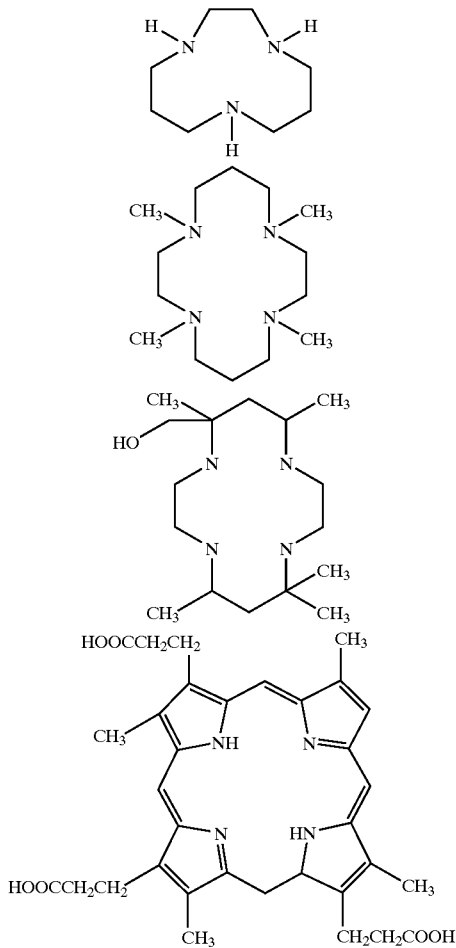

For example, monoamines may include: triethylamine, tripropylamine, tribenzylamine, 1-methyl-2-piperidinemethanol, and N,N-diethylethanolamine ($HOCH_2CH_2N(C_2H_5)_2$).

It should be understood that the complexing agents listed are examples only. Many other complexing agents, not listed, may be used in the process of the invention.

The process of the present invention provides a method for endpoint detection for wet copper stripping. This saves time, cost, and materials. The invention adds a colorimetric or spectrophotometric detector to analyze the eluent from the stripping chamber. Novel compounds/chemicals are added to the stripping chemicals. These chemicals react with the copper being stripped. Thus, the detector can detect when all the copper is removed and signal a stop to the stripping process.

While the invention has been particularly shown and described with reference to the preferred embodiments thereof, it will be understood by those skilled in the art that various changes in form and details may be made without departing from the spirit and scope of the invention.

What is claimed is:

1. A method of stripping copper from a wafer in the fabrication of an integrated circuit comprising;
   providing a wafer having a layer of copper thereon;
   stripping copper from said water using wet copper stripping chemicals in a chamber wherein an eluent is produced and sent from said chamber to a drain wherein said eluent is not re-circulated back into said chamber;

continuously analyzing said eluent on its way to said drain by colorimetric or spectrophotometric analysis for decreasing amounts of copper; and stopping said copper stripping process when said copper is no longer detected in said eluent.

2. The method according to claim 1 wherein said decreasing amounts of said copper is detected by a reaction of said copper with an indicator added to said wet copper stripping chemicals.

3. The method according to claim 2 where said indicator comprises Fast Sulphon Black F indicator and an ammonium ion-containing solution.

4. The method according to claim 2 where said indicator comprises a complexing agent wherein said complexing agent increases a spectroscopic absorption coefficient of said wet copper stripping chemicals.

5. The method according to claim 3 wherein said ammonium ion-containing solution is selected from the group consisting of: ammonium acetate, ammonium carbonate, ammonium hydroxide, ammonium nitrate, ammonium perchlorate, ammonium sulfate, ammonium tetrafluoroborate, ammonium trifluoroacetate, ammonium trifluoromethanesulfonate [$NH_4(CF_3SO_3)$], and a mixture of ammonium fluoride, water, and ethylenediamine.

6. The method according to claim 4 wherein said complexing agent is selected from the group consisting of: diamines, amine macrocycles, and monoamines.

7. The method according to claim 6 wherein said complexing agent is a diamine and is selected from the group consisting of: $H_2NCH_2CH_2N(C_2H_5)_2$ (ethylenediamine), $(C_2H_5)_2NCH_2CH_2N(C_2H_5)_2$, (N,N,N',N'-5 tetraethylenediamine),

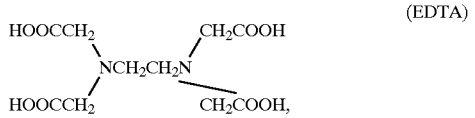

(EDTA)

1,10-phenanthroline, and 2,2'-bipyridine-4,4'-dicarboxylic acid.

8. The method according to claim 6 wherein said complexing agent is an amine macrocycle.

9. The method according to claim 6 wherein said complexing agent is a monoamine and is selected from the group consisting of: triethylamine, tripropylamine, tribenzylamine, 1-methyl 2-piperidinemethanol, and N,N-diethylethanolamine ($HOCH_2CH_2N(C_2H_5)_2$).

10. The method according to claim 8 wherein said amine macrocycle is 1,4,8-triazacycloundecane.

11. The method according to claim 8 wherein said amine macrocycle is 1,4,8,11-tetramethyl-1,4,8,11-tetraazacyclotetradecane.

12. The method according to claim 8 wherein said amine macrocycle is 3,8,13,18-tetramethyl-21H,23H-porphine-2,7,12,17-tetrapropionic acid dihydrachloride.

13. A method of stripping copper from a wafer comprising:

providing a wafer having a layer of copper thereon;

stripping copper from said wafer using wet copper stripping chemicals in a chamber wherein an eluent is produced and sent from said chamber to a drain wherein said eluent is not re-circulated back into said chamber;

continuously analyzing said eluent on its way to said drain by colorimetric analysis for decreasing amounts of copper; and stopping said copper stripping process when said copper is no longer detected in said eluent.

14. The method according to claim 13 wherein said decreasing amounts of said copper is detected by a reaction of said copper with an indicator added to said wet copper stripping chemicals.

15. The method according to claim 14 where said indicator comprises Fast Sulphon Black F indicator and an ammonium ion-containing solution.

16. The method according to claim 14 where said indicator comprises a complexing agent wherein said complexing agent increases a spectroscopic absorption coefficient of said wet copper stripping chemicals.

17. The method according to claim 15 wherein said ammonium ion-containing solution is selected from the group consisting of: ammonium acetate, ammonium carbonate, ammonium hydroxide, ammonium nitrate, ammonium perchlorate, ammonium sulfate, ammonium tetrafluoroborate, ammonium trifluoroacetate, ammonium trifluoromethanesulfonate [$NH_4(CF_3SO_3)$], and a mixture of ammonium fluoride, water, and ethylenediamine.

18. The method according to claim 16 wherein said complexing agent is selected from the group consisting of: diamines, amine macrocycles, and monoamines.

19. The method according to claim 16 wherein said complexing agent is a diamine and is selected from the group consisting of: $H_2NCH_2CH_2N(C_2H_5)_2$ (ethylenediamine), $(C_2H_5)_2NCH_2CH_2N(C_2H_5)_2$, (N,N,N',N'-5 tetraethylenediamine),

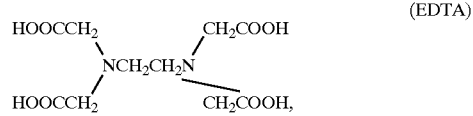

(EDTA)

1,10-phenanthroline, and 2,2'-bipyridine-4,4'-dicarboxylic acid.

20. The method according to claim 16 wherein said completing agent is an amine macrocycle.

21. The method according to claim 16 wherein said complexing agent is a monoamine and is selected from the group consisting of: triethylamine, tripropylamine, tribenzylamine, 1-methyl 2-piperidinemethanol, and N,N-diethylethanolamine ($HOCH_2CH_2N(C_2H_5)_2$).

22. A method of stripping copper from a wafer comprising:

providing a wafer having a layer of copper thereon;

stripping copper from said wafer using wet copper stripping chemicals in a chamber wherein an eluent is produced and sent from said chamber to a drain wherein said eluent is not re-circulated back into said chamber;

continuously analyzing said eluent on its way to said drain by spectrophotometric analysis for decreasing amounts of copper; and stopping said copper stripping process when said copper is no longer detected in said eluent.

23. The method according to claim 22 wherein said decreasing amounts of said copper is detected by a reaction of said copper with an indicator added to said wet copper stripping chemicals.

24. The method according to claim 23 where said indicator comprises Fast Sulphon Black F indicator and an ammonium ion-containing solution.

25. The method according to claim 23 where said indicator comprises a complexing agent wherein said complexing agent increases a spectroscopic absorption coefficient of said wet copper stripping chemicals.

26. The method according to claim 24 wherein said ammonium ion-containing solution is selected from the group consisting of: ammonium acetate, ammonium carbonate, ammonium hydroxide, ammonium nitrate, ammonium perchlorate, ammonium sulfate, ammonium tetrafluoroborate, ammonium trifluoroacetate, ammonium trifluoromethanesulfonate [$NH_4(CF_3SO_3)$], and a mixture of ammonium fluoride, water, and ethylenediamine.

27. The method according to claim 25 wherein said complexing agent is selected from the group consisting of: diamines, amine macrocycles, and monoamines.

28. The method according to claim 25 wherein said complexing agent is a diamine and is selected from the group consisting of: $H_2NCH_2CH_2N(C_2H_5)_2$ (ethylenediamine), $(C_2H_5)_2NCH_2CH_2N(C_2H_5)_2$, (N,N,N', N'-5 tetraethylenediamine),

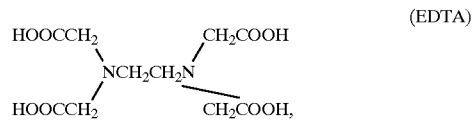

1,10-phenanthroline, and 2,2'-bipyridine-4,4'-dicarboxylic acid.

29. The method according to claim 25 wherein said complexing agent is an amine macrocycle.

30. The method according to claim 25 wherein said complexing agent is a monoamine and is selected from the group consisting of: triethylamine, tripropylamine, tribenzylamine, 1-methyl 2-peridinemethanol, and N,N-diethylethanolamine ($HOCH_2CH_2N(C_2H_5)_2$).

31. The method according to claim 29 wherein said complexing agent is selected from the group consisting of: 1,4,8-triazacycloundecane, 1,4,8,11-tetramethyl-1,4,8,11-tetraazacyclotetradecane, and 3,8,13,18-tetramethyl-21H, 23H-porphine-2,7,12,17-tetrapropionic acid dihydrochloride.

* * * * *